(12) United States Patent
Ramasamy et al.

(10) Patent No.: US 6,613,896 B1
(45) Date of Patent: Sep. 2, 2003

(54) METHOD OF PRODUCING TIAZOFURIN AND OTHER C-NUCLEOSIDES

(75) Inventors: Kandasamy Ramasamy, Laguna Hills, CA (US); Rajanikanth Bandaru, Irvine, CA (US); Devron Averett, Irvine, CA (US)

(73) Assignee: ICN Pharmaceuticals, Inc., Costa Mesa, CA (US)

( * ) Notice: Subject to any disclaimer, the term of this patent is extended or adjusted under 35 U.S.C. 154(b) by 0 days.

(21) Appl. No.: 09/445,713

(22) PCT Filed: Jun. 25, 1998

(86) PCT No.: PCT/US98/13367

§ 371 (c)(1),
(2), (4) Date: Jun. 6, 2000

(87) PCT Pub. No.: WO99/00399

PCT Pub. Date: Jan. 7, 1999

Related U.S. Application Data (60) Provisional application No. 60/051,191, filed on Jun. 30, 1997.

(51) Int. Cl.[7] .............................. C07H 7/06; C07H 5/04
(52) U.S. Cl. ........................ 536/29.2; 536/18.7; 514/23; 514/183; 514/359; 514/360
(58) Field of Search .......................... 514/23, 183, 359, 514/360; 536/29.2, 18.7

(56) References Cited

U.S. PATENT DOCUMENTS 4,531,001 A * 7/1985 Robins et al. .............. 536/26.9
5,907,036 A * 5/1999 Ramasamy et al. ........ 536/55.3

OTHER PUBLICATIONS

Hennen et al., Journal of Organic Chemistry, vol. 50, pp. 1741–1746, 1985.*

* cited by examiner

*Primary Examiner*—James O. Wilson
*Assistant Examiner*—Howard V. Owens, Jr.
(74) *Attorney, Agent, or Firm*—Rutan & Tucker, LLP; Robert D. Fish (57) ABSTRACT

C-nucleosides are synthesized by a method in which a sugar is derivatized in a single step to provide a heterocycle at the $C_1$ position, and then the heterocycle is aromatized in another single step. In one class of preferred embodiments a cyano sugar is converted into thiocarboxamide, and subsequently condensed to form an azole ring. In a second class of preferred embodiments a cyano sugar is condensed with an amino acid to provide the azole ring. In a third class of preferred embodiments a halo sugar is condensed with a preformed heterocycle to provide the azole ring.

21 Claims, 3 Drawing Sheets

METHOD OF PRODUCING TIAZOFURIN AND OTHER C-NUCLEOSIDES

This application is a 371 of PCT/US98/13367 filed Jun. 25, 1998 which claims benefit of Ser. No. 60/051,191 filed Jun. 30, 1997, now expired.

BACKGROUND

C-Nucleosides are interesting compounds having potential activity as pharmaceutical agents. One of these compounds, Tiazofurin, [6,2-(β-D-ribofuranosyl)thiazole-4-carboxamide)], possesses significant activity against both human lymphoid. F. Earle and R. I. Glazer, *Cancer Res.*, 1983, 43 133), lung tumor cell lines (D. N. Camex, G. S. Abluwalia, H. N. Jayaram, D. A. Cooney and D. G. Johns, *J. Clin. Invest.*, 1985, 75 175) and murine-implanted human ovarian cancers (J. P. Micha, P. R. Kucera, C. N. Preve, M. A. Rettenmaier, J. A. Stratton, P. J. DiSaia, *Gynecol. Oncol.* 1985, 21, 351). Tiazofurin also demonstrated efficacy in the treatment of acute mycloid leukemia (G. T. Tricot, H N. Jasyaram C. R. Nichols, K. Pennington, E. Lapis, G. Weber and R. Hoffman, *Cancer Res.* 1997, 47 4988). In addition, recent findings has brought interest in Tiazofurin as a possible treatment for patients with chronic myeloid leukemia (CML) in blast crisis (G. Weber, U.S. Pat. No. 5,405, 837; 1995). In the cells Tiazofurin is converted to its active metabolite, thiazole-4-carboxaimde adenine dinucleotide (TAD) which inhibits IMP dehydrogenase, and as a result depletes guanosine nucleotide pools. (E. Olah, Y. Natusmeda, T. Ikegami, Z. Kote, M. Horanyi, I Szelenye, E. Paulik, T. Kremmer, S. R. Hollan, J. Sugar and G. Weber, *Proc. Natl. Acad. Sci. USA*, 1988, 85, 6533).

Although Tiazofurin has been known for over 15 years, and is currently under phase II/III trials in humans, there is no suitable synthesis for large scale production. Tiazofurin was first synthesized independently by M. Fuertes et al. (*J. Org. Chem.*, 1976, 41, 4076) and Srivastava et al. (*J. Med. Chem.*, 1977, 20, 256) in low yield. In both methods the authors obtained side products (i.e. compound 12) and used column chromatography at each stage to purify the products. The principal disadvantage of these methods is the formation of the furan derivative as well as the utility of highly toxic hydrogen sulfide gas.

W. J. Hannon et al. (*J. Org. Chem.*, 1985, 50, 1741) developed a somewhat different route for Tiazofurin in 19% yield. The Hannon method also suffers from low yield, the use $H_2S$ gas and chromatographic purifications. More recently P. Vogel et al. (*Helv. Chem. Acta.*, 1989, 72, 1825) synthesized Tiazofurin in nine steps with 25% yield. Still more recently, D. C. Humber et al. (*J. Chem. Soc. Perkin Trans. 1*, 1990, 283) worked a synthesis for Tiazofurin starting from benzyl (2,3,5-tri-O-benzoyyl-β-D-ribofuranosyl) penicillinate.

The only known method that is at all suitable for large scale production is by Parsons et al (U.S. Pat. No. 4,451, 684). Unfortunately, the Parsons method uses both mercury cyanide and hydrogen sulfide, both of which have safety and environmental problems. The Parsons method also gives a mixture of products.

The problems discussed above which attend large scale production of Tiazofurin are applicable to large scale production of other C-nucleosides. In the production of thiocarboxamides, for example, most of the known methods use gaseous hydrogen sulfide as a reagent to convert a cyano group into a corresponding thicarboxamide group. Such methods have inherent environmental problems. In production of C-nucleosides in general, most or all of the known syntheses give a mixture of products during a ring closure step. Thus, there is a continuing need for a new procedure for large scale production of Tiazofurin and other C-nucleosides.

SUMMARY OF THE INVENTION

The present invention is directed to a novel method for synthesizing C-nucleosides, in which the $C_1$ position of a sugar is derivatized in a single step to provide a heterocycle, and then the heterocycle is aromatized in another single step.

In one class of preferred embodiments a cyano sugar is converted into thiocarboxamide, and subsequently condensed to form an azole ring. In a second class of preferred embodiments a cyano sugar is condensed with an amino acid to provide the azole ring. In a third class of preferred embodiments a halo sugar is condensed with a preformed heterocycle to provide the azole ring.

There are many advantages to the present method. One advantage is that the method eliminates the need for gaseous hydrogen sulfide, which is environmentally unsafe. Another advantage is that the yield is substantially improved over previous methods. A third advantage is that the present method eliminates the need for chromatographic purification procedures, thereby reducing the cost of production.

These and various other objects, features, aspects and advantages of the present invention will become more apparent from the following detailed description of preferred embodiments of the invention, along with the accompanying drawings in which like numerals represent like components.

DETAILED DESCRIPTION

Figure 1:
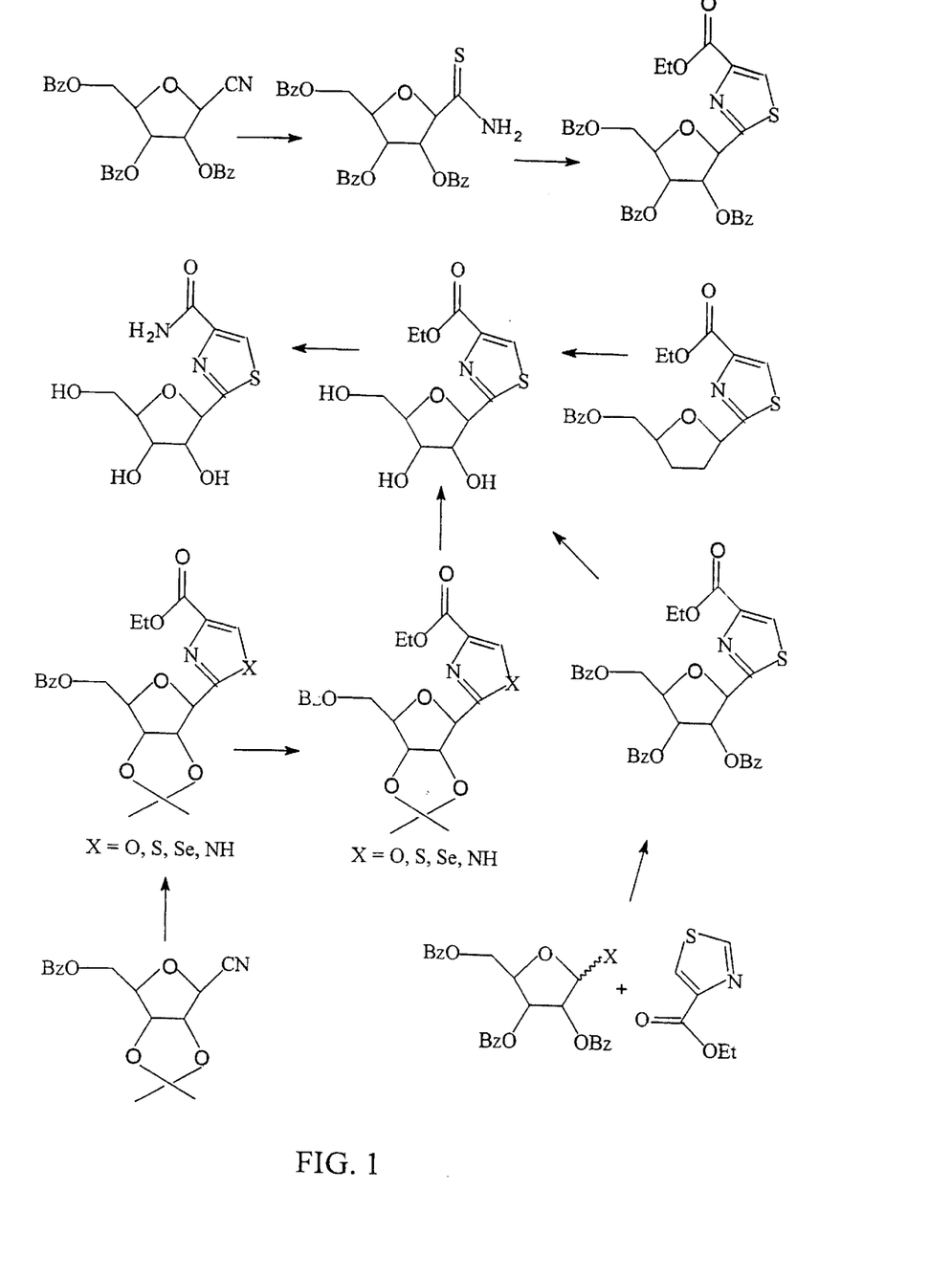
FIG. 1 is a series of reaction schemes demonstrating various embodiments of the present invention.
Figure 2:
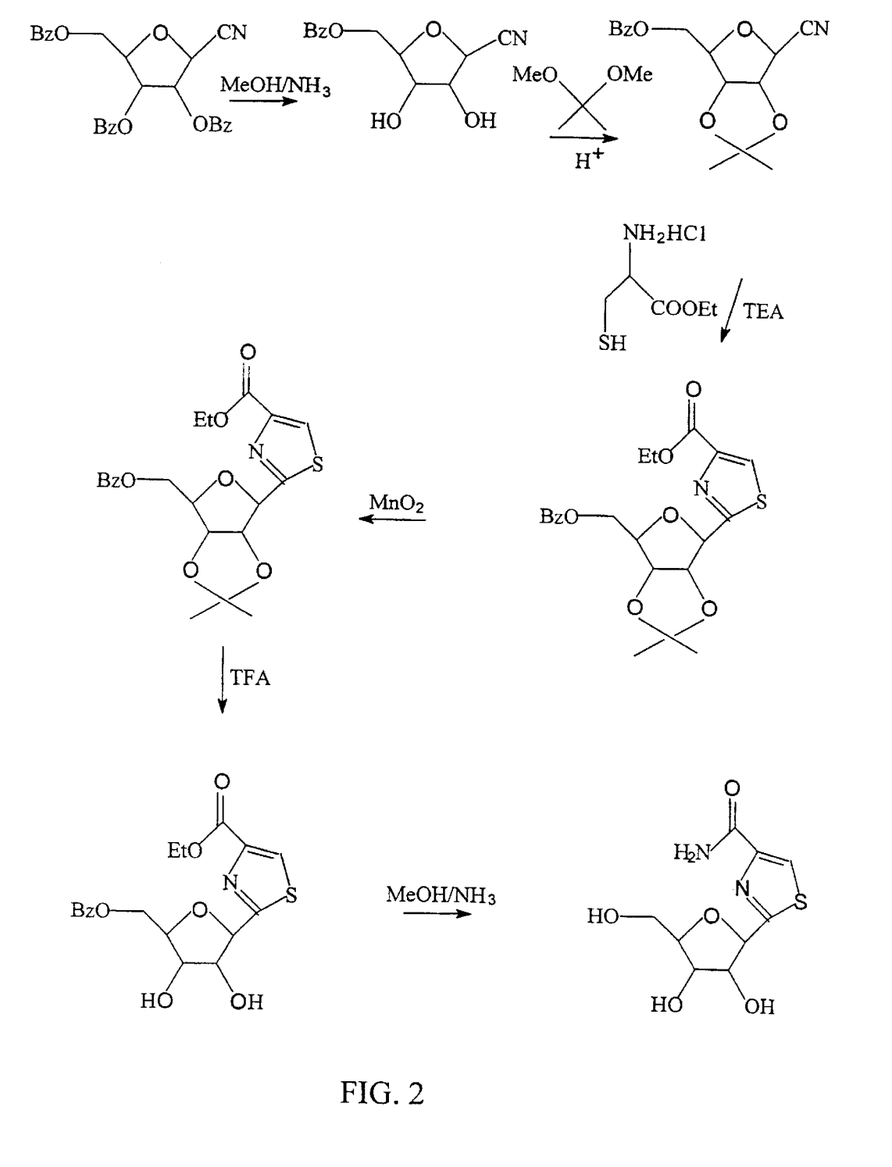
FIG. 2 is another series of reaction schemes demonstrating various embodiments of the present invention.
Figure 3:
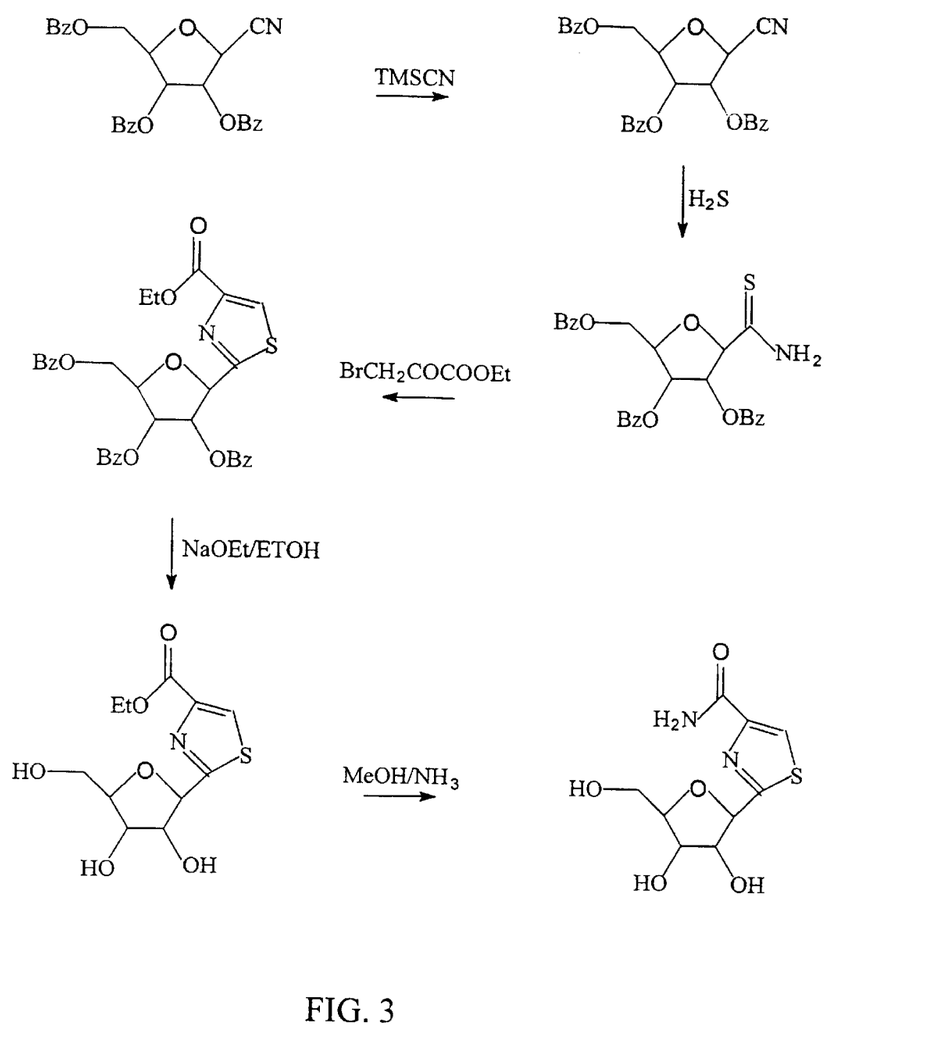
FIG. 3 is another series of reaction schemes demonstrating various embodiments of the present invention.

There are three preferred classes of methods for executing the present invention, each of which is exemplified with respect to production of Tiazofurin in FIGS. 1, 2 and 3.

In one preferred class of embodiments, a cyano sugar is converted into thiocarboxamide, and subsequently condensed to form an azole ring. In the particular example shown in FIG. 1, a blocked cyano sugar (2) is converted into thiocarboxamide (3), and subsequently condensed with ethylbromopyruvate to give a Tiazofurin intermediate (4). The process shown provides Tiazofurin in quantitative yield without any side products (12 or the α-anomer of 4).

In a second class of preferred embodiments a cyano sugar is condensed with an amino acid to provide the azole ring. In the particular example shown in FIG. 2, a known cyano (8) is condensed with cysteine ethyl ester hydrochloride to give the ring closed product (9), which is then aromatized with activated manganese dioxide to provide the Tiazofiurin intermediate (10). This key intermediate (10) is conveniently transformed into Tiazofurin in good yield.

In a third class of preferred embodiments a halo sugar is condensed with a preformed heterocycle to provide the azole ring. In the particular example shown in FIG. 1, a preformed heterocycle (13) is condensed with a known halo-sugar (14) to provide the key intermediate (4) from which Tiazofurin can be readily derived.

Of course, the inventive methods disclosed herein are not limited to production of Tiazofurin, and may be readily generalized, including especially generalization of the second and third classes of methods to virtually all C-nucleosides. In general, a C-nucleoside according to the present invention falls within the general structure A, where A is O, S, $CH_2$ or NR where: R is H or a blocking group; X is O, S, Se or NH; $R_1$, $R_2$, $R_3$ and $R_4$ are independently H or lower alkyl; and $Z_1$, $Z_2$ and $Z_3$ are independently H or non-H,

Structure A

To achieve the various compounds comprehended by structure A, there may be considerable variability in the sugar portion of the molecule. Among other things, sugar itself need not be a simple furan. For example, the oxygen may be replaced with sulphur to form a thio-sugar, or nitrogen to form an amino-sugar. In addition, the sugar can be substituted at the C2', C3' and C4' positions with a group other than hydrogen. Still further, the sugar can have a D- or L-configuration, and may be an alpha- or beta-anomer. Still further, the sugar may have blocking groups at various stages in the synthesis. All of these permutations are comprehended by Structure B, where A is O, S, $CH_2$ or NR where R is H or a blocking group; $B_1$, $B_2$, and $B_3$ are independently blocking groups or lower alkyl, and $Z_1$, $Z_2$ and $Z_3$ are independently H or non-H. The group L is a reactive functionality such as CN, halogen or CHO.

Structure B

Focusing again on the second class of preferred embodiments, the use of cysteine ethyl aster hydrochloride can be generalized to the use of a compound according to Structure C, where X is O, S, Se or NH; Y is H or lower alkyl; and $R_4$ is H or lower alkyl.

Structure C

Similarly, in the third class of preferred embodiments, the use of a preformed heterocycle may be generalized to the use of a compound according to Structure D, where $R_4$ is H or lower alkyl.

Structure D

There are, of course, numerous blocking groups which would be appropriate. Among other things, one may use benzoyl, benzyl, silyl, or isopropylidene. In addition, it is specifically contemplated that the blocking groups at the C2' and C3' positions on the sugar may be formed into a isopropylidene group, as shown in Structure E.

Structure E

This isopropylidene group can be removed by many processes, including by treatment with a reagent selected from the group consisting of trifluoroacetic acid, formic acid, acetic acid, an $H^+$ resin in an organic solvent, or iodine in methanol. Applying the present method to Structure E may then give a compound according to Structure F, where R5 is H, lower alkyl, amine or aryl.

Structure F

The embodiment also includes the aromatization of structure F with activated manganese dioxide or other reagents and followed by deblocking of the protecting groups to provide Tiazofurin or related C-nucleosides.

Especially preferred embodiments according to the inventive subject matter herein include Reaction A or Reaction B, shown below.

Reaction A

Reaction B

These and other features may be appreciated by the following working examples, which are to be interpreted as being illustrative of various aspects of the claimed subject matter, but not limiting as to the scope of the claimed subject matter.

EXPERIMENTAL

EXAMPLE I 2,3,5-Tri-O-benzoyl-β-D-ribofuranosyl-1-carbonitrile (2): A mixture of 1-O-acetyl-2,3,5-tri-O-benzoyl-b-D-ribofuranose (dried at 60° C., 1 mm, 12 h) (630 g, 1.249 mol), trimethylsilyl cyanide (dried over molecular sieves, 24 h) (250 mL, 1.875 mol), and dichloromethane (dried over magnesium sulfate and stored over molecular sieves) (1.25 L) was stirred and cooled to 0–2° C. Stannic chloride (50 mL, 0.425 mol) was added slowly 1(1.5 h) while maintaining a reaction temperature of 0–2° C. and resulting mixture was stirred and maintained at −5 to 0° C. for an additional 1.5 h. The reaction mixture was added slowly (30 min.) and vigorous stirring to a cold (5° C.) 10% sodium hydroxide solution (1.5 L) which was maintained at 5–8° C. throughout the addition. The layers were separated and the organic layer was washed with water (3×500 mL) until neutral and then dried over anhydrous magnesium sulfate (approx. 150 g). The mixture was filtered and the drying agent was washed with dichloromethane (3×500 mL). The filtrate, and washings were combined and the solution was concentrated (<30° C., 20 mm) to a volume of 2–2.5 L. The remaining solution was filtered through a bed (13.5 cm id×6.5 cm) of Silica Gel and the bed was further eluted with dichloromethane (2.5 L). The dichloromethane solutions were combined and evaporated (<30° C., 20 mm) to a syrup (approx. 750 mL). The syrup was mixed with ethanol (1.5 L) and the mixture was heated (approx. 60° C.) to obtain a homogenous solution. Seed crystals of 2,3-anhydro-3,4,6-tri-O-benzoyl-b-D-allononitrile were added and the solution was stirred at ambient temperature for 2 h and then slowly cooled to 0° C. over a 2 h period. The crystalline solid was collected, washed with cold (−5° C.) ethanol (3×600 mL), washed with hexanes (600 niL), and dried at 45° C. and 1 mm for 12 h; 452 g (0.959 mol, 76%), mp 73–75° C. (lit mp 78–80° C.). $^1$H NMR (DMSO-d$_6$): d 4.61 (m, 2), 4.80 (q, 1), 5.88 (t, 1), 6.05 (t, 1), 7.45–7.57 (m, 6), 7.64–7.71 (m, 4), 7.88–7.94 (m, 4), and 8.07 (d, 2).

EXAMPLE 2

2,5-Anhydro-3,4,6-tri-O-bensoyl-D-allonthioamide (3): Method A: Hydrogen sulfide was passed through a cold (5° C.) stirred suspension of 2',3',5'-tri-O-benzoyl-β-D-ribofliranosyl cyanide (, 50 g. 106.16 mmol) in dry EtOH (900 ml) for 5 min, then N,N-dimethylaminopyridine (1.2 g, 10 mmol) was added in one portion. Hydrogen sulfide was slowly passed through the stirred reaction mixture for 5 hr (the outlet tube from the reaction flask was bubbled through bleach solution made in 5% NaOH). After 5 hr, the flask was sealed and stirring continued below 25° C. for 16 hr. Argon was passed through the reaction mixture for 1 h to remove the last traces of H$_2$S. The suspension was stirred at 0° C. for 2 hr and the solid separated was filtered, washed with cold dry EtOH and dried over P$_2$O$_5$ at vacuum. Yield 52 g (97%); mp 133–135° C. $^1$H NMR (CDCl$_3$): δ 4.72 (m, 2H) 4.74 (m, 1 H), 5.12 (d, 1 H), 5.71 (t, 1 H), 5.98 (t, 1 H), 7.30–7.60 (m, 10 H), 7.86 (d, 2 H), 8.14 (m, 4 H) and 8.46 (bs, 1H).

Method B: A solution of 2',3',5'-tri-O-benzoyl-β-D-ribofuranosyl cyanide (2, 4.71 g, 10.00 mmol) and thioacetamide (1.50 g, 20.00 mmol) in dry DMF (50 ml) was saturated with anhydrous hydrogen chloride and heated at 70–60° C. for 2 hr. The reaction was cooled and evaporated to dryness. The residue was dissolved in methylene chloride (150 ml), washed with Sat. NaHCO$_3$ solution (100 ml), water (100 ml) and brine (70 ml). The organic extract was dried over anhydrous MgSO4, filtered and washed with CH$_2$Cl$_2$ (50 ml). The combined filtrate was evaporated to dry ness. The residue was dissolved in minimum amount of dry ethanol which on cooling gave pure product Yield 4.20 g (83%). The mp and spectral characteristics of this product agreed with the product prepared in the previous Method A.

EXAMPLE 3

Ethyl 2-(2',3',5'-tri-O-benzoyl-β-D-ribofuranosyl)thiazole-4-carboxylate (4): To a stirred mixture of 2,5-anhydro-3',4',6'-tri-O-benzoyl-D-allonthioamide (3, 10.12 g, 20.00 mmol) and solid NaHCO$_3$, (16.8 g, 200 nunol) in dry 1,2-dimethoxyethane (60 ml) at 0° C. under argon atmosphere was added ethyl bromopyruvate (7.8 g, 40.00 mmol) during 10 min period. After the addition, the reaction mixture was stirred at 0° C. under argon for 6 hr. TLC indicated complete conversion of the starting material into a single product (Hex: EtOAc, 7:3). The reaction was cooled to −15° C. in dry ice/CCl$_4$ under argon. A solution of trifluoroacetic anhydride (12.6g, 60.00 mmol) and 2,6-lutidine (12.8.4 g, 120 mmol) dissolved in dry 1,2- dimethoxyethane (20 ml) was added slowly during 15 min period. After the addition, the reaction was stirred at −15° C. for 2 hr under argon atmosphere. The reaction mixture was filtered, washed with dry methylene chloride (100 ml). The combined filtrate was evaporated to dryness under reduced pressure. The residue was dissolved in $CH_2Cl_2$ (200 ml) and the pH was adjusted to 7 with sat. $NaHCO_3$ solution. The organic extract was washed with 1N HCl (100 ml), sat. $NaHCO_3$ (200 ml) and brine (100 ml). The organic layer was dried over anhydrous $Na_2SO_4$, filtered, washed with $CH_2Cl_2$ (100 ml) and evaporated to dryness. The crude material was used as such for further reaction. A small quantity was purified by flash chromatography over silicagel using hexane-ethyl acetate as the eluent. $^1H$ NMR ($CDCl_3$): δ 1.36 (t, 3 H), 4.40 (m, 2 H), 4.62 (dd, I H), 4.74 (m, 1 H), 4.86 (dd, I H), 5.74 (d, I H), 5.84 (m, 2 H), 7.30–7.60 (m, 9 H 7.91 (d, 2 H), 7.98 (d, 2 H), 8.08 (m, 2 H and 8.12 (s, I H).

EXAMPLE 4

Ethyl 2-(β-D-ribofuranosyl)thiazole-4-carboxylate (5): The crude ethyl-(2',3',5'-tri-O benzoyl-β-D-ribofiuranosyl)thiazole-4-carboxylate (4, 15.00 g) was dissolved in dry ethanol (100 ml) and treated with sodium ethoxide powder (1.36 g, 20 mmol) under argon atmosphere. The reaction mixture was stirred at room temperature for 12 hr under argon. The solution was neutralized with Dowex 50W-X8 $H^+$ resin, filtered and washed with methanol (100 ml). The filtrate was evaporated to dryness. The residue was partitioned between water (100 ml) and chloroform (I50 ml). The aqueous layer was washed with chloroform (100 ml) and evaporated to dryness. The residue was dissolved in methanol (100 ml), silica gel (15 g) was added and evaporated to dryness. The dried compound adsorbed silica gel was placed on top of the silica column (5×20 cm) packed in $CH_2Cl_2$. The column was eluted with $CH_2Cl_2$/acetone (7:3; 500 ml) followed by $CH_2Cl_2$/methanol(95:5; 1000 ml). The $CH_2Cl_2$/methanol fractions were collected together and evaporated to give pure 5. A small amount was crystallized from 2-propanol/ether as colorless product. Yield 4.8 g (83%); mp 62–64° C. $^1H$ NMR (DMSO-$d_6$); δ 1.36 (t, 3 H), 3.52 (m; 2 H), 3.84 (m, 2 H), 4.06 (m, I H), 4.28 (m, 2 H), 4.94 (t, 1H), 4.98 (d, 1 H), 5.08 (d, I H), 5.46 (d, I H) and 8.52 (s, 1 H).

EXAMPLE 5

2-β-D-Ribofuranosylthiazole-4-carboxamide (Tiazofurin) (6): The crude ethyl 2-(β-ribofuranosyl)thiazole-4-carboxylate (E, 4.6 g, 15.92 mmol) was placed in a steel bomb and mixed with freshly prepared methanelic ammonia (saturated at 0° C., 70 ml). The reaction mixture was stirred at room temperature for 12 hr. The steel bomb was cooled, opened careftilly and the content evaporated to dryness. The residue was triturated with dry ethanol (60 ml) and evaporated to dryness. The residue was treated with dry ethanol (60 ml) which on trituration gave light yellow solid. The solid was filtered, washed with ethyl acetate and dried. The solid was crystallized from ethanol/ethyl acetate to gave pure product. Yield 3.6 g (87%); mp142–144° C., $^1H$ NMR (DMSO-$d_6$): δ 3.57 (m, 2 H), 3.89 (bs, 2 H), 4.06 (m, I H), 4.84 (t, 1 H), 4.93 (d, I H), 5.06 (m, I H), 5.37 (d, 1 H), 7.57 (s, I H), 7.69 (s, I H) and 8.21 (s. I H).

EXAMPLE 6

5-O-Benzoyl-β-D-ribofuranosyl-1-carbonitrile (7): A solution of 2',3',5'-tri-O-benzoyl-β-D-ribofuranosyl-1-carbonitrile (2, 61 g, 129.40 mmol) in chloroform (200 ml) was added with stirring into an ice-cold saturated dry methanolic ammonia (500 ml) under argon atmosphere. The reaction mixture was stirred at 0° C. for 4.5 hr. TLC indicated complete conversion of the starting material. The reaction mixture was evaporated to dryness. The residue was dissolved in ethyl acetate (500 ml), washed with sat. $NaHCO_3$, solution (100 ml), water (300 ml) and brine (150 ml). The organic extract was dried over anhydrous $MgSO_4$, filtered, washed with ethyl acetate, (100 ml) and the filtrates are combined, and evaporated to dryness to provide a dark brown liquid. The liquid was dissolved in benzene (100 ml), diluted with hexane (50 ml) and acetone (15 ml). The solution on standing at room temperature overnight gave crystals. The solid was filtered, washed with hexane and dried. Yield 29 g (85%); mp 116–117° C.

EXAMPLE 7

5-O-Benzoyl-2,3-O-isopropylidene-β-D-riboftiranosyl-1-carbonitrile (: Solid 5'-O benzoyl-β-D-ribofuranosyl-1-carbonitrile (2, 26.3 g, 100 mmol) was added to a stirring solution of 72% percholoric acid (4 ml) in 2,2-dimethoxypropane (30 ml) and dry acetone (150 ml) under argon atmosphere in one portion. The reaction mixture was stirred at room temperature for 3 hr. The solution was neutralized with ammonium hydroxide and evaporated to dryness. The resdue was dissolved in chloroform (250 ml) and washed with water (2×200 ml) and brine (100 ml). The organic phase was dried over anhydrous $MgSO_4$, filtered, washed with chloroform (50 ml) and the filtrate evaporated to dryness. The residue on crystallization from ether-hexane gave colorless crystals. Yield 28.5 g (95%); mp 62–63° C. $^1H$ NMR ($CDCl_3$) δ:1.35 (s. 3 H), 1.52 (s, 3 H), 4.51 (m, 2 H), 4.59 (m, 2 H), 4.77 (d, I H), 4.87 (d, I H), 5.10 (m, I H), 7.46 (m, 2 H), 7.57 (m, 1 H) and 8.07 (m, 2 H).

EXAMPLE 8

Ethyl 2-(5'-O-Benzoyl-2',3'-O-isopropylidene-β-D-riboffuranosyl)thiazoline-4-carboxylate (9): To a stirred solution of 5'-O-Benzoyl-2',3'-O-isopropylidene-β-D-ribofuranosyl-1-carbonitrile (8, 4.71 g, 15.55 mmol) in dry methylene chloride, (150 ml) at room temperature under argon atmosphere was added cysteine ethyl ester hydrochloride (1.49 g, 8 nmuol) and (0.81 g, 8 mmol) at 0 hr, 2nd hr, 4th hr and 6th hr. The reaction mixture was stirred at room temperature under argon atmosphere for 24 hr. The reaction was diluted with methylene chloride (100 ml), washed with water (200 ml) and brine (150 ml). The $CH_2Cl_2$ extract was dried over anhydrous $MgSO_4$,filtered, washed with $CH_2Cl_2$ (50 ml) and the filtrate evaporated to dryness. The residue was used as such for the next reaction. A small amount of the crude product was purified by flash chromatography over silica gel using hexane/ethyl acetate as eluent and characterized by proton spectroscopy. $^1H$ NMR ($CDCl_3$): δ 1.24 (t, 3 H), 1.35 (s, 3 H), 1.52 (s, 3 H), 3.40 (m, 2 H), 4.20 (m, 2 H), 4.42 (m, 3 H), 4.80 (m, 2 H), 5.12 (m, 2 H), 7.42 (m, 2 H), 7.58 (m, 1 H) and 8.08 (m, 2 H).

EXAMPLE 9

Ethyl 2-(5'-O-Benzoyl-2',3'-O-isopropylidene-β-D-ribofuranosyl) thiazole-4-carboxylate (10):

Method A: To a vigorously stirred solution of the crude ethyl 2-(5'-O-Benzoyl-2', 3'-O-isopropylidene-β-D-ribofuranosyl)thiazoline-4-carboxylate (9,7.0 g) in methylene chloride (300 ml) was added activated manganese dioxide (27.8 g) at room temperature. The reaction mixture was stirred at room temperature for 24 hr, filtered through celite and washed with acetone (200 ml). The filtrates were combined and evaporated to dryness to give an oily residue. Yield 5.9 g (88% from the cyano sugar O. A small amount of the crude product was purified by flash chromatography over silica gel using $CH_2Cl_2$-ethyl acetate as eluent and characterized by proton spectroscopy. $^1$H NMR ($CDCl_3$): δ 1.39 (t, 6 H), 1.63 (s, 3 H), 4.39 (m, 3 H), 4.60 (m, 2 H), 4.84 (m, I H), 5.26 (m, 1 H), 5.40 (d, 1 H), 7.40 (m, 2 H), 7.52 (m, 1 H), 7.89 (m, 2 H) and 8.02 (s, 1 H).

Method B: A mixture of the crude ethyl 2-(5'-O-Benzoyl-2', 3'-O-isopropylidene-β-D-ribofuranosyl)thiazoline-4-carboxylate (9, 7.0 g) and activated manganese dioxide (27.8 g) in dry benzene (150 ml) was heated at 80° C. for 2 hr. The reaction mixture was filtered through celite and washed with acetone (200 ml). The filtrates were combined and evaporated to dryness to give an oily residue. Yield 6.0 g (89% from the cyano sugar 8). A small amount of the crude product was purified by flash chromatography over silica gel using $CH_2Cl_2$-ethyl acetate as eluent and by proton spectroscopy. The products obtained by both methods were found to be identical in all respects.

Method C: To a vigorously stirred solution of the crude ethyl 2-(5'-O-Benzoyl-2', 3'-O-isopropylidene-β-D-ribofuranosyl)thiazoline-4-carboxylate (9, 2.0 g) in methylene chloride (100 ml) was added nickel peroxide (10.0 g) at room temperature. The reaction mixture was stirred at room temperature for 24 hr, filtered through celite and washed with acetone (200 ml). The filtrates were combined and evaporated to dryness to give an oily residue. Yield 5.9 g(88% from the cyano sugar 8). The product obtained by this method was found to be identical with products obtained by the methods A and B in all respects.

EXAMPLE 10

Ethyl 2-(5'-O-Benzoyl-β-D-ribofuranosyl)thiazole-4-carboxylate (11): A solution of the crude ethyl 2-(5'-O-Benzoyl-2',3'-O-isopropylidene-β-D-ribofuranosyl)thiazole-4-carboxylate (10, 4.5 g, 10.39 mmol) in a mixture of trifluoroacetic acid:tetrahydroftiran:water (30:20:6 ml) was allowed to stir at room temperature for 1hr. The reaction mixture was evaporated to dryness. The residue was suspended in methylene chloride (100 ml), cooled and neutralized with sat. $NaHCO_2$ solution. The aqueous solution was extracted with $CH_2Cl_2$ (2×100 ml), washed with sat. $NaHCO_3$ solution (100 ml), water (100 ml) and brine (100 ml). The organic extract was dried over MgSO4, filtered, washed with $CH_2Cl_2$ (100 ml) and the filtrate evaporated to dryness. The residue, was crystallized from ethanol/water (1:1) to give colorless crystals. The solid was filtered and dried over $P_2O_5$ under vacuum. Yield 4.0 g (98%); mp 82–85° C. $^1$H NMR ($CDCl_3$): δ 1.33 (t, 3 H), 4.31 (m, 4 H), 4.45 (m, 3 H), 4.55 (m, 1 H), 4.74 (m, 1 H), 5.32 (d, 1 H), 7.37 (m, 2 H), 7.51 (m, 1 H) and 7.99 (m, 3 H).

EXAMPLE 11

2-β-D-Ribofuranosylthiazole-4-carboxamide (Tiazoflirin) (6): Ethyl 2-(5'-O-Benzoyl-β-D-ribofuiranosyl)thiazole-4-carboxylate (11, 3.7 g, 942 mmol) was placed in a steel bomb and mixed with freshly prepared cold methanolic ammonia (70 ml, saturated at 0° C. The mixture was protected from moisture and stirred at room temperature for 12 hr. The steel bomb was cooled to 0° C., opened carefully and evaporated to a sticky foam. The residue was triturated with dry toluene (3×50 ml) and the toluene layer was discarded. The residue that obtained was treated with anhydrous ethanol (60 ml) and triturated to give light yellow solid. The solid was filtered, washed with ethyl acetate and dried. The solid was crystallized from ethanol-ethyl acetate to provide 2.25g (90%) of pure product: mp 145–147° C. $^1$H NMR (DMSO-$d_6$): δ 3.57 (M,2 H), 3.89) (s,2 H), 4.07(m, 1 H), 4.83 (t, 1H), 4.92 (d, 1H), 5.05 (d, 1 H), 5.36 (d, 1 H), 7.56 (s, 1), 7.69 (s, 1) and 8.20 (s,1).

Thus, specific embodiments and applications of a method of producing Tiazoflrin and other C-Nucleosides have been disclosed. It should be apparent, however, to those skilled in the art that many more modifications besides those already described are possible without departing from the inventive concepts herein. The inventive subject matter, therefore, is not to be restricted except in the spirit of the appended claims.

We claim:

1. A method of synthesizing a nucleoside according to Structure A, comprising:
   providing a compound according to Structure B wherein L is a reactive group selected from the group consisting of CN, CHO, or halogen;
   in a single step reacting L of Structure B to form Structure D having a heterocyclic ring; and
   in a single step aromatizing the heterocyclic ring;

Structure A

Structure B

Structure D wherein the step of reacting L of Structure B to form Structure D comprises reacting Structure B with Structure C

Structure C wherein A is O, S, $CH_2$, or NR where R is H or a blocking group; X is O, S, Se or NH;
$R_1$, $R_2$, $R_3$, and $R_4$ are independently H or lower alkyl; $B_1$, $B_2$, and $B_3$ are independently blocking groups or lower alkyl, and $Z_1$, $Z_2$, and $Z_3$ are independently H or non-H.

2. The method of claim 1 wherein the compound according to Structure B is Structure E Structure E 3. The method of claim 2 wherein the step of reacting L to form Structure D comprises reacting Structure E with Structure C, wherein Y is H or lower alkyl Structure C 4. The method of claim 1 wherein the step of replacing L comprises Reaction A Reaction A

5. The method of claim 1 wherein L is replaced with Structure D.

6. The method of claim 5 further comprising reacting the compound with a reagent selected from the group consisting of an amino acid and a substituted amino acid to produce an intermediate according to Structure F, where $R_5$ is H, lower alkyl, amine, or aryl Structure F 7. The method of claim 6 wherein the amino acid is a cysteine alkyl ester hydrochloride.

8. The method of claim 6 further comprising aromatizing the compound of Structure F Structure F

9. The method of claim 6 wherein the step of aromatizing comprises treating the compound of Structure F with activated manganese dioxide Structure F 10. The method of claim 1 wherein the step of reacting L comprises Reaction B Reaction B 1. Ethylbromopyruvate/ NaHCO3
2. TFFA/2,6-lutidine 11. The method of claim 9 wherein the compound according to Structure F contains an isopropylidene group, and the isopropylidene group is removed by treatment with a reagent selected from the group consisting of trifluoroacetic acid, formic acid, acetic acid, an $H^+$ resin in an organic solvent, or iodine in methanol.

12. The method of claim 1 wherein the nucleoside is Tiazofurin.

13. The method of claim 1 wherein the compound of Structure B comprises an L-ribose.

14. The method of claim 13 wherein at least one of $Z_1$, $Z_2$, and $Z_3$, is not H.

15. The method of claim 1 wherein the compound of Structure B is an alpha isomer.

16. The method of claim 1 wherein the compound of Structure B is a beta isomer.

17. The method of claim 1 wherein A is NR, R is $COCH_3$, and X is not S.

18. A compound produced by the method of claim 1, and having a structure according to Structure A, wherein the sugar portion is an alpha isomer, other than Tiazofurin.

19. A compound produced by the method of claim 1, and having a structure according to Structure A, wherein the sugar portion has an L configuration.

20. A compound produced by the method of claim 1, and having a structure according to Structure A, wherein the sugar portion is an alpha isomer.

21. A compound produced by the method of claim 1, and having a structure according to Structure A, wherein at least one of $Z_1$, $Z_2$, and $Z_3$, is not H.

* * * * *